United States Patent [19]

Balazs

[11] 4,303,676
[45] Dec. 1, 1981

[54] HYALURONATE BASED COMPOSITIONS AND COSMETIC FORMULATIONS CONTAINING SAME

[76] Inventor: Endre A. Balazs, 3333M Henry Hudson Pkwy., Riverdale, N.Y. 10463

[21] Appl. No.: 133,481

[22] Filed: Mar. 21, 1980

[51] Int. Cl.$^3$ ............... A61K 47/00; A01N 25/00
[52] U.S. Cl. ............... 424/359; 424/361; 424/362; 424/365; 424/180
[58] Field of Search ............... 424/180, 361, 362, 359, 424/177, 365, 358; 536/4

[56] References Cited

U.S. PATENT DOCUMENTS

| | | | |
|---|---|---|---|
| 3,659,025 | 4/1972 | Halleck | 424/180 |
| 4,141,973 | 2/1979 | Balazs | 536/4 |
| 4,151,304 | 4/1979 | Evans | 424/361 |

OTHER PUBLICATIONS

Chemical Abstracts, vol. 91, 1979, p. 332, Abstract No. 216677c, Ito, K., "Cosmetics".
Chemical Abstracts, vol. 91, 1979, p. 223, Abstract No. 15532c, Endo, M., et al., "Isolation and characterization of proteohyaluronic acid from human umbilical cord".

*Primary Examiner*—Delbert R. Phillips
*Assistant Examiner*—Blondel Hazel
*Attorney, Agent, or Firm*—Berger & Palmer

[57] ABSTRACT

A water based, viscoelastic composition for use in cosmetic formulations comprising, (a) a mixture of sodium hyalfractions having different molecular weights, (b) protein which is derived from the natural material from which the hyaluronate is obtained, and (c) water. Also disclosed are cosmetic formulations comprising about 0.05–5.0% of the above composition together with an emollient, a sugar alcohol, a neutral or anionic polysaccharide, a preservative, bacteriostatic and fungistatic substance which does not react with or degrade hyaluronic acid, and water.

10 Claims, 2 Drawing Figures

HYALURONATE BASED COMPOSITIONS AND COSMETIC FORMULATIONS CONTAINING SAME

CROSS-REFERENCE TO RELATED APPLICATIONS

None

BACKGROUND OF THE INVENTION

1. Field of the Invention

The present invention relates to hyaluronate based compositions and cosmetic formulations.

2. The Prior Art

Hyaluronic acid (hereinafter referred to as "HA") as well as its salts, such as sodium hyaluronate (hereinafter referred to as "NaHA") is a known, naturally occurring high viscosity glycosaminoglycan having alternating $\beta$ 1-3 glucuronidic and $\beta$ 1-4 glucosaminidic bonds. The molecular weight of this material is generally within the range of 50,000 to 8,000,000 (although there are reports of HA having molecular weights as high as 13,000,000) depending on the source, method of isolation and method of determination. It is found in animal tissue, e.g. in umbilical cord, vitreous humor, synovial fluid, rooster combs, pathologic joints, group A and C hemolytic streptococci and in skin.

The isolation and characterization of HA is described in Meyer et al, J. Biol. Chem. 107, 629 (1934); J. Biol. Chem. 114, 689 (1936); Balazs, Fed. Proc. 17, 1086 (1958); Laurent et al; Biochim. Biophys. Acta 42, 476 (1960). The structure of HA was elucidated by Weissman et al, J. Am. Chem. Soc. 76, 1753 (1954) and Meyer, Fed. Proc. 17, 1075 (1958).

For certain uses, extremely pure HA preparations are required; see, for example my U.S. Pat. No. 4,141,973, which describes the preparation and uses of such an HA.

It is also known that the softness and flexibility of the stratum corneum, which is the upper layer of the skin, depends on the moisture content of the intercellular channels in this layer. Thus, cosmetic chemists and medical researchers have, long sought to find ways of restoring these vital qualities of the skin when they are lost, as occurs with the natural aging process, and in cases of extreme dryness.

SUMMARY OF THE INVENTION

Figure 1:
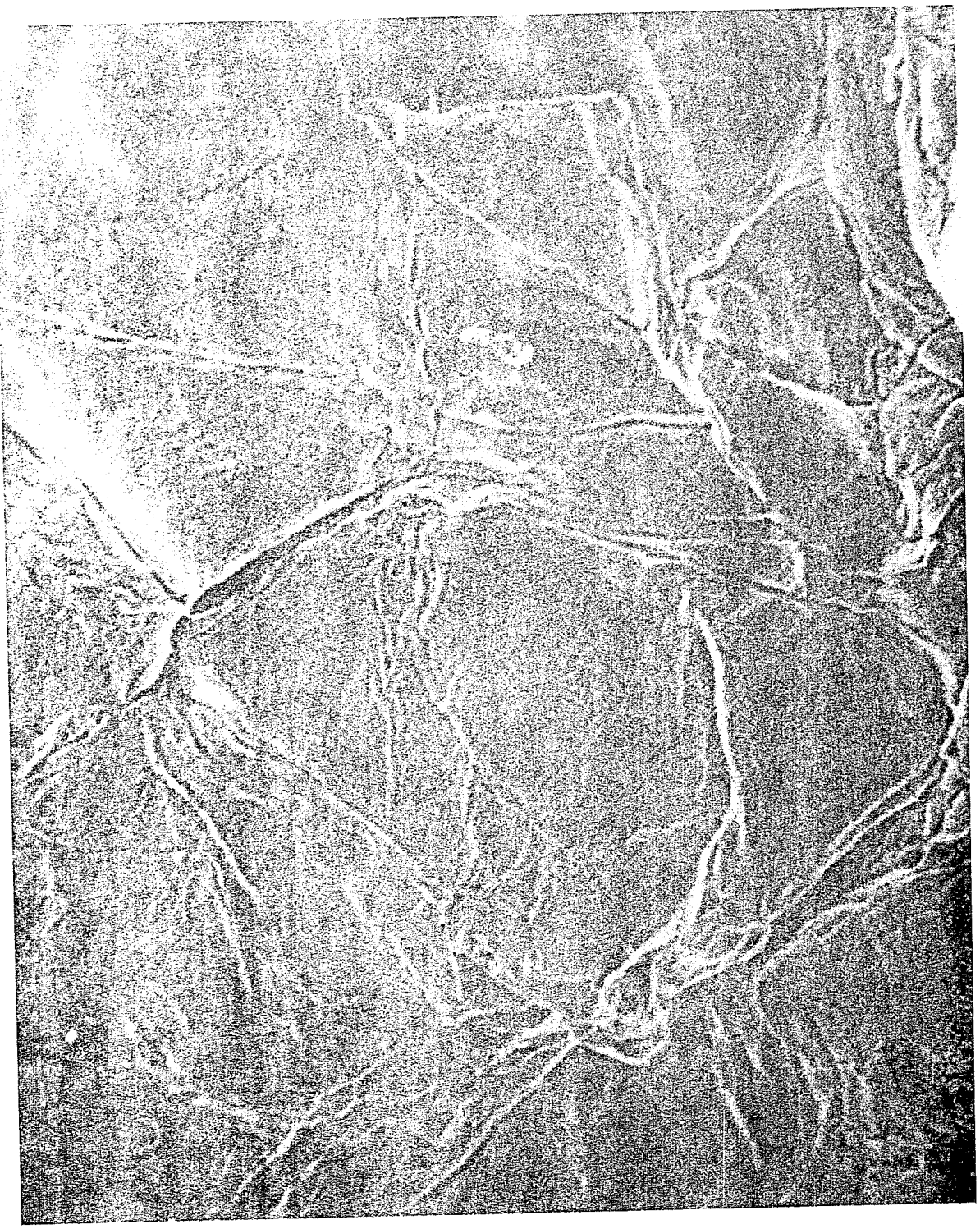
FIG. 1 is a photomicrograph taken with a scanning electron microscope of the skin of a mouse which has been treated with the composition according to the invention.

The present invention provides, in one aspect thereof, a water-based, highly viscoelastic composition based on hyaluronate and which is useful as a base for cosmetic formulations. The composition has emollient, moisturizing, elasticizing and lubricating properties when applied to the skin. The composition according to the invention comprises a mixture of two different molecular weight hyaluronate fractions, a low molecular weight (10,000–200,000) and a high molecular weight ($1 \times 10^6$–$4.5 \times 10^6$) fraction, the ratio between the two being 0.3–2:1. The composition also includes protein in an amount ranging from 50% to 400% of the weight of the hyaluronate, said protein being derived from the natural material from which the hyaluronate is obtained, e.g., rooster combs. The remainder of the composition is water.

In another aspect, the invention provides cosmetic formulations comprising 0.05 to 5.0% of the above composition together with emollients, subtances for increasing the viscoelasticity of the hyaluronate, preservative, bacteriostatic and fungistatic substances and water. For esthetic appeal, a fragrance can also be added.

DETAILED DESCRIPTION OF THE INVENTION

The principal active ingredient of the composition of the invention, which for convenience sake I call HPE (hyaluronate protein elestogel), is obtained from rooster combs, living tissue known to be relatively rich in hyaluronic acid. Of course, being a natural living tissue, it also contains numerous proteins.

To obtain HPE, a batch of rooster combs is homogenized, minced or simply cut into small sections after being thoroughly washed with water. The washed and homogenized rooster combs are then extracted with water under constant stirring. The weight ratio of combs to water is typically about 1:4, that is, about 3.75 liters of water for every kilogram of combs, although this ratio may, of course, vary. The extracting solution should also have bacteriostatic agents added thereto. Examples of such bacteriostatic agents include chloroform, cetylpyridinium chloride and propylparaben. After the extraction procedure is completed, the tissue (combs) is separated from the fluid, for example, by filtration, centrifugation or decantation. The extract contains, inter alia, Na—HA and various proteins. The extract is then precipitated using ethanol or acetone and the like; or it can be lyophilized.

The HPE which is obtained as a result of the above procedure was determined to have the following properties:

(a) The ratio, by weight, of Na—HA to protein is about 1:0.5–4.0;

(b) the molecular weight of the NaHA is in the range of $1 \times 10^6$ to $4.5 \times 10^6$; and (c) aqueous solutions of from 0.05 to 5.0% are in the form of highly visco-elastic gels.

It will be noted that the molecular weight of this preparation is such that it can be used, as such, as the high molecular weight fraction of the composition. The low molecular weight fraction is obtained by subjecting a portion of the above preparation to a heat treatment whereby the NaHA is partially degraded. Thus, in a typical case, an aqueous solution of the high molecular weight HPE (concentration=0.5 to 1.0%) is placed in a sealed glass container and heated at 100° C. for 0.5–2.0 hours, as a result of which, the NaHA is partially degraded so as to have a molecular weight of about 30,000–200,000. The protein content, and therefore, the ratio of NaHa/protein, remains the same as in the undegraded HPE preparation.

It has been found that the higher the molecular weight (and thus, the viscosity) of an HPE preparation, the greater the degree of penetration into the skin. Thus, a high molecular weight HPE will only penetrate the very outermost layer of the skin while a very low molecular weight HPE (on the order of about 30,000) will penetrate much more deeply into the skin.

Human skin consists of two layers: an outer layer called the stratum corneum and below that, an inner layer called the stratum Malphigi. The stratum Malphigi contains the first layer of living epithelial cells. The stratum corneum is only a few microns thick; stated in other terms, it is about 10-20 cells in thickness. The outermost of these 10-20 cells are, for all intents and purposes, dead cells. The innermost of these 10-20 cells are living tissue, i.e., those closest to the stratum Malphigi. Those in between are in varying stages of cell "death" and as new cells are regenerated in the stratum Malphigi, there is a constant sloughing off of the outer, or dead cells. As part of the natural aging process, the rate at which old and dying cells in the stratum corneum are replaced by newly generated cells in the stratum Malphigi decreases and this accounts, at least in part, for the aging appearance of aging skin.

The composition according to the invention (as well as cosmetic formulations based thereon) can thus be varied with respect to its visco-elasticity so as to be suited for use on skin of varying ages in accordance with the degree of skin penetration desired.

In addition to its ability to penetrate the skin, the HPE, because of another of its properties is readily able to maintain the surface of the skin in a well lubricated condition. The phenomenon is explained below.

Because of the highly hydrated nature of the sodium hyaluronate molecule, HPE retains water in amounts many times its own dry weight when it is dried at various humidities.

To determine the extent of this, the water retaining capacity of aqueous solutions of HPE was studied. Small volumes (0.5-1.0 ml) of HPE which contained 0.1-1.0% Na—HA (MW $1 \times 10^6$–$4 \times 10^6$) and 0.1-1.0% protein were kept in dessicators at constant temperature (22°-25° C.) and constant humidity (47 and 70% relative humidity). The water content of HPE/gram Na—HA was determined until constant weight conditions were achieved.

The following table shows the grams of water retained by 1 gram of NaHA:

| Time (days) | 70% Humidity | | 47% Humidity | |
| --- | --- | --- | --- | --- |
| | not autoclaved* | autoclaved** | not autoclaved* | autoclaved** |
| 1 | 388 | 339 | 340 | 276 |
| 4 | 195 | 165 | 17 | 14 |
| 5 | 98 | 82 | 11 | 9 |
| 7 | 22 | 27 | 10 | 8 |
| 11 | 22 | 26 | 9 | 8 |

*Sample not sterilized
**Sample sterilized by heat (autoclave, 120° C. for 12 minutes)

Results: The NaHA in HPE releases water very slowly, taking 5-7 days to reach constant weight. When no more water is released the large Ha—HA molecules retain 22-27 times their own weight of water at 70% humidity and 8-10 times their own weight of water at 47% humidity. This means that when HPE dries on the skin at room temperature it will contain approximately 8-27 times more water than its own dry weight. Consequently, on the surface and partially filling the micro-channels of the stratum corneum, HPE maintains a moist layer through which normal skin metabolites can pass relatively freely.

BIOLOGICAL ACTIVITY

I. The Effect of HPE on the Skin of the Hairless Mouse

The effect of HPE on the skin surface of the hairless mouse was evaluated using scanning electron microscopy. Four hairless mice were treated daily for 30 days with either 2% HPE or 2% HPE in which the hyaluronic acid had been broken down by heat degradation (D-HPE) to yield a solution which had a viscosity close to that of water. One side of the back of each mouse was treated with HPE and the other with D-HPE.

As shown in FIG. 1 (HPE) the surfaces of the mouse skin cells have relatively smooth outlines and relatively few cracks and folds.

Figure 2:
FIG. 2 is a photomicrograph taken with a scanning electron microscope of the skin of a mouse which has been treated with a heat degraded composition which is otherwise identical to that of FIG. 1.

For comparative purposes, as seen in FIG. 2, (D-HPE), the surface of the cells have many cracks and folds.

These results suggest that long HPE treatment changed the skin surface in such a way that when the skin was dried (which is necessary for visualization in the electron microscope) it retained its smooth surface structure while the control (D-HPE) did not. The difference clearly can only be due to the HPE treatment.

II. Toxicity Studies a. Oral Toxicity Test

HPE is prepared from the skin of animals which have been slaughtered for human consumption. During the purification procedure no toxic chemicals are used, and all other chemicals which are used during this process are removed. Therefore oral toxicity studies are deemed not to be necessary.

b. Skin Toxicity Test

HPE was applied to half the dorsal skin of four (4) hairless mice daily for 30 days. During this time the skin was observed for redness, thickening and scaling. At the end of this 30-day period electron microscope studies were carried out on the treated skin.

During and after the 30-day treatment, no abnormalities of any kind could be observed. It was concluded that HPE, which contains animal proteins and sodium hyaluronate, is not irritative or immunologically active when applied to the skin of another animal species.

c. Eye Toxicity Test

Ten (10) albino rabbits (3.0 kg) were used for this test. One drop of HPE was instilled into the conjunctival sac of the right eye, while the left eye received 1 drop of 0.9% saline instilled in the same manner. The eyes were then examined (using a slit lamp) for any pathological changes of the cornea, iris, and conjuctiva after 48 hours.

None of the above-mentioned eye-tissues showed inflammation or irritation. No difference between the HPE-treated eyes and the control eyes could be seen by an unbiased observer.

DESCRIPTION OF THE PREFERRED EMBODIMENT

The HPE composition according to the invention, in its preferred embodiment, is as follows:

It is a white to yellow, non-transparent sterile liquid solution having a pH of 6 to 7.5 and containing about 1% sodium hyaluronate and 0.5 to 1.5% protein. The balance 97.5 to 98.5% is water. The sodium hyaluronate is comprised of a low molecular weight (10-50,000) fraction and a high molecular weight ($1 \times 10^6$–$4.5 \times 10^6$) fraction in a ratio of 0.3-2:1). The composition is highly visco-elastic; however, if it is desired to increase the visco-elasticity, this can be accomplished by lowering the pH to as low as about 2.5 with concentrated HCl.

The cosmetic formulations according to the invention which are based on the above described HPE composition contain, in addition to the HPE composition, emollients, various substances for increasing the visco-elasticity of the hyaluronate and preservative, bacteriostatic and fungistatic substances which do not react with a degrade HA. The bulk of the cosmetic formulation is water, and of course, one or more fragrances can be added for purely esthetic purposes.

Among the emollients, squalene is preferred, although others may also be used. For example, isopropyl myristate or isopropyl linoleate may be used.

Among the substances for increasing the visco-elasticity, it is preferred to use at least one sugar alcohol such as sorbitol or mannitol and the like. In addition, the formulation also includes neutral or anionic polysaccharides (which also increase the visco-elasticity). The preferred polysaccharide is methocellulose (methylated carboxycellulose). Other high molecular weight polysaccharides such as pectins, alginates and carageenins may also be used.

The preservative, bacteriostatic and fungistatic substance is any preservative which does not react with or degrade HA. The preferred substance is propyl-p-hydroxybenzoate, although any other water soluble hydroxybenzate may also be used. Finally, in the most preferred embodiment of the cosmetic formulation, a small amount of a fragrance is added.

The formulation according to the invention comprises about 0.05-5.0% of the above HPE composition, about 1-5% of the emollient, about 1-5% of the sugar alcohol, about 0.2-1% of the neutral or anionic polysaccharide and about 0.05-2% of the preservative, the balance being distilled water.

In its most preferred embodiment, the formulation is as follows:
HPE; 0.2 gm
squalene; 3 ml
sorbitol; 1.0 gm
methocel; 0.5 gm
propyl p-hydroxybenzoate; 0.12 gm
fragrance (Huile de Fleur); 8 drops
distilled water; 98 ml Variations and modifications can, of course, be made without departing from the spirit and scope of the invention.

Having thus described my invention what I desire to secure by Letter Patent and hereby claim is:

1. A water based, viscoelastic composition comprising, by weight, (a) a mixture of different sodium hyaluronate fractions, a first such fraction having a molecular weight of about 10,000 to 200,000 and a second fraction having a molecular weight of about $1 \times 10^6$ to $4.5 \times 10^6$, the ratio of said fractions being in the range of about 0.3-2:1, (b) about 50 to 400% of protein based on the weight of ingredient (a), said protein being derived from the natural material from which the hyaluronate is obtained, and (c) the balance being water.

2. A composition according to claim 1 having a pH of about 6-7.5.

3. A composition according to claim 1 and further comprising sufficient concentrated hydrochloric acid to lower the pH to about 2.5.

4. A composition according to claim 1 wherein the water is distilled water.

5. A cosmetic formulation comprising, by weight, about 0.05-5.0% of the composition as claimed in claim 1, about 1-5% of an emollient, about 1-5% of a sugar alcohol, about 0.2-1% of a neutral or anionic polysaccharide, about 0.05-2% of a preservative, bacteriostatic and fungistatic substance which does not react with or degrade hyaluronic acid, the balance to make up 100% being distilled water.

6. A formulation according to claim 5 wherein the emollient is squalene, isopropyl myristate or isopropyl linoleate.

7. A formulation according to claim 5 wherein the sugar alcohol is sorbitol or mannitol.

8. A formulation according to claim 5 wherein the neutral or anionic polysaccharide is methylated carboxycellulose, pectin, alginate or carageenin.

9. A formulation according to claim 5 when the preservative substance is propyl p-hydroxybenzoate or any other water soluble hydroxybenzoate.

10. A formulation according to claim 5 and further comprising a fragrance.

* * * * *

UNITED STATES PATENT AND TRADEMARK OFFICE
CERTIFICATE OF CORRECTION

PATENT NO. : 4,303,676
DATED : December 1, 1981
INVENTOR(S) : Endre A. Balazs

It is certified that error appears in the above-identified patent and that said Letters Patent are hereby corrected as shown below:

Column 2, line 64: "higher" should read --lower--

Signed and Sealed this

Seventeenth Day of May 1983

[SEAL]

Attest:

DONALD J. QUIGG

Attesting Officer     Acting Commissioner of Patents and Trademarks